United States Patent [19]
Hart

[11] Patent Number: 5,388,600
[45] Date of Patent: Feb. 14, 1995

[54] STACKABLE FLOSSER

[75] Inventor: Adrian Hart, Menlo Park, Calif.

[73] Assignee: Gillette Canada, Inc., Kirkland, Canada

[21] Appl. No.: 118,370

[22] Filed: Sep. 8, 1993

[51] Int. Cl.6 ............................................. A61C 15/00
[52] U.S. Cl. .................................................... 132/323
[58] Field of Search ............... 132/321, 323, 324, 325, 132/326, 327, 329; 206/581, 369, 63.5

[56] References Cited

U.S. PATENT DOCUMENTS

| | | | |
|---|---|---|---|
| D. 274,375 | 6/1984 | Tomlin | D28/64 |
| D. 298,176 | 10/1988 | Davis | D28/64 |
| D. 333,002 | 2/1993 | Tarrson et al. | D24/133 |
| 3,247,857 | 4/1966 | Kanbar | 132/93 |
| 3,311,116 | 3/1967 | Foster | 132/325 |
| 3,871,392 | 3/1975 | Thomas | 132/323 |
| 3,918,466 | 11/1975 | Peebles | 132/323 |
| 3,943,949 | 3/1976 | Ashton et al. | 132/89 |
| 3,981,989 | 9/1976 | Suganuma et al. | 424/50 |
| 4,006,750 | 2/1977 | Chodorow | 132/323 |
| 4,041,962 | 8/1977 | Johansson et al. | 132/91 |
| 4,583,564 | 4/1986 | Finkelstein et al. | 132/91 |
| 4,645,662 | 2/1987 | Nakashima et al. | 424/52 |
| 4,832,062 | 5/1989 | Grollimund et al. | 132/327 |
| 4,974,615 | 12/1990 | Doundoulakis | 132/321 |
| 4,986,288 | 1/1991 | Kent et al. | 132/321 |
| 5,076,300 | 12/1991 | Mayfield | 132/321 |
| 5,113,880 | 5/1992 | Honda et al. | 132/321 |
| 5,127,415 | 7/1992 | Preciutti | 132/323 |
| 5,183,064 | 2/1993 | Barth | 132/323 |
| 5,184,632 | 2/1993 | Gross et al. | 132/326 |
| 5,184,719 | 2/1993 | Gordon | 206/209.1 |
| 5,246,021 | 9/1993 | Katz | 132/323 |

FOREIGN PATENT DOCUMENTS

| | | | |
|---|---|---|---|
| 735125 | 11/1932 | France | 132/323 |
| 3920256 | 2/1990 | Germany | 132/323 |
| 1342182 | 12/1973 | United Kingdom | 132/323 |
| 2222089A | 2/1990 | United Kingdom | 132/323 |

Primary Examiner—Cary E. O'Connor
Attorney, Agent, or Firm—Chester Cekala

[57] ABSTRACT

The present invention relates generally to a flosser-type tooth cleaning device comprised of a handle, a holder affixed to an end of the handle comprised of two protruding arm members positioned at least parallel to each other, and a strand of dental floss which is drawn between the arms and anchored at the distal end of each arm, wherein of these several tooth cleaning device may be non-permanently held together forming an inter-locking stack. The flossers of the present invention may be held non-permanently in a stacked configuration by way of a friction fit or a snap-lock mechanism.

17 Claims, 5 Drawing Sheets

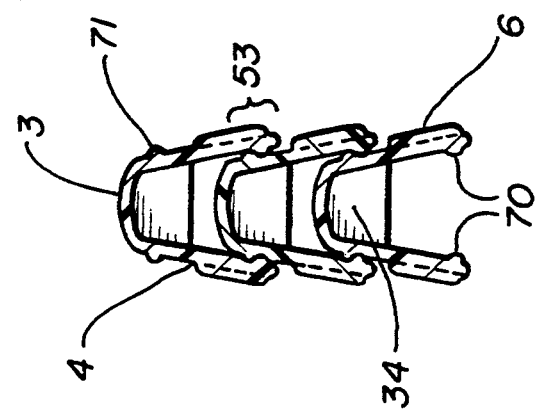
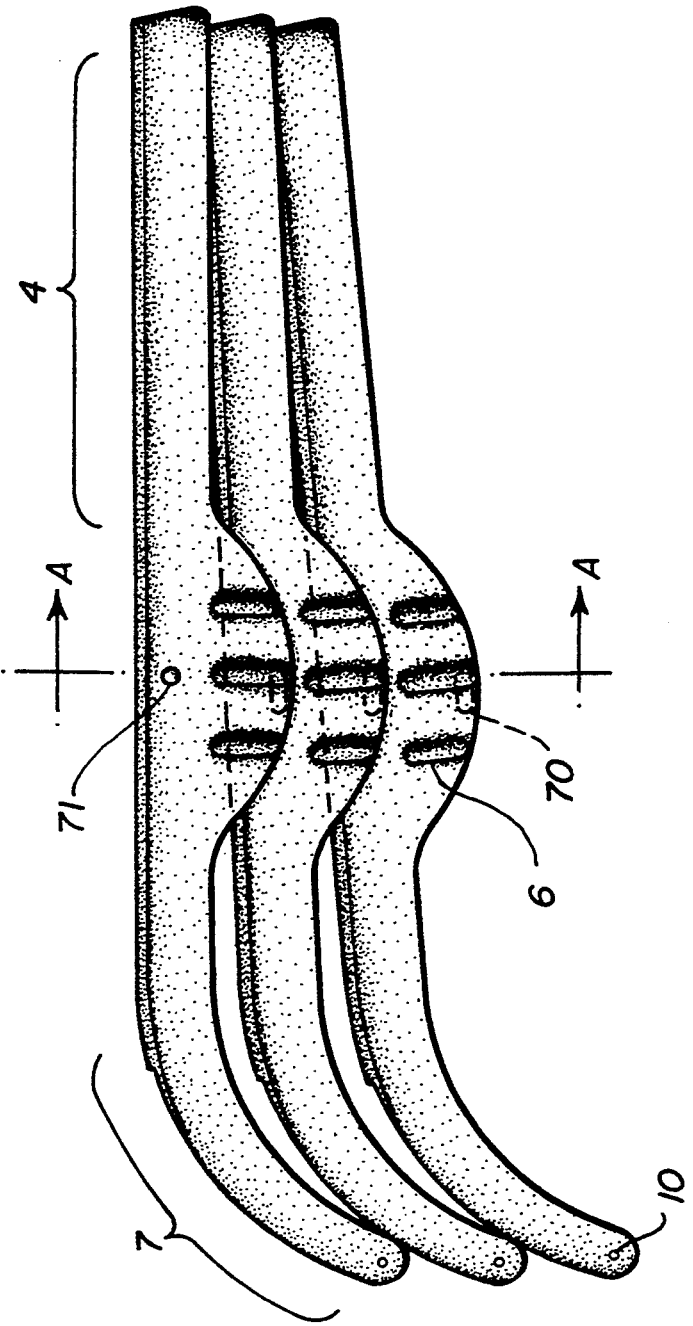

STACKABLE FLOSSER

FIELD OF THE INVENTION

The invention relates to a tooth cleaning device with a handle, on which a holder with two arms is provided, between which arms a thread-shaped strand of dental floss runs.

BACKGROUND

A flossing thread, or dental floss, is used for cleaning between adjacent teeth. A single strand of floss is usually held in tension between the fingers of a person whose teeth are being cleaned, or else between a pair of spaced mechanical elements projecting from a common supporting handle. In either case, the common practice is to insert a strand between the adjacent teeth and to rub it up and down against the adjacent side of one tooth while pulling in one direction against that side, and thereafter against the adjacent side of the other tooth while pulling in the opposite direction against the other side.

Devices which utilize spaced mechanical elements in place of human fingers as described above are commonly referred to as "flossers". Flossers generally consist of a handle with two arm-like members projecting from one end of the handle, between the arms, a strand of dental floss runs. See, for example, U.S. Pat. Nos.: 4,041,962; 4,832,062; 5,113,880; 5,127,415; 5,183,064; 5,184,632; 5,184,719; U.K. Pat. No. 2,222,089; PCT Application PCT/US92/03259; and U.S. Design Pat. Nos. 274,375 and 298,176.

Flossers are typically sold in bulk. Packages containing 4 to 20 flosser are common in the industry. Unfortunately, commercially available flossers fit awkwardly into common box type packaging. Furthermore, when individual flossers are removed from a package, the remaining flossers become disarrayed and tangled. This disarray can cause the flosser to become tangled or cause the floss to become frayed due to wear. If the flossers are removed from their bulk package, they do not store neatly in a pocket, purse or brief case.

Accordingly, it is an object of the present invention to provide flossers which stack neatly, one on top of the other.

It is also an object of the present invention to provide a stackable flossers which lock together to form an integral stack from which individual flossers can be removed.

Other objects, advantages and features of the invention will become apparent as the following more detailed disclosure proceeds.

SUMMARY OF THE INVENTION

The present invention relates generally to a tooth cleaning device comprised of a handle, a holder affixed to an end of the handle comprised of two protruding arm members positioned at least parallel to each other and a strand of dental floss which is drawn between the arms and anchored at the distal end of each arm, wherein several tooth cleaning device may be stacked in "nesting fashion" one on top of another.

BRIEF DESCRIPTION OF DRAWINGS

Present preferred embodiments of the invention are shown in the accompanying drawings, which show, for purposes of illustration only, the following figures:

FIG. 8 is a side view of a stack of three flossers. The broken-lined regions depicting the snap-fit mechanism, 70 and 71, of the preferred embodiment.

FIG. 9 is a cross-sectional view of the stack of FIG. 8 cut along line A—A.

DETAILED DESCRIPTION OF THE PRESENT INVENTION

Figure 1:
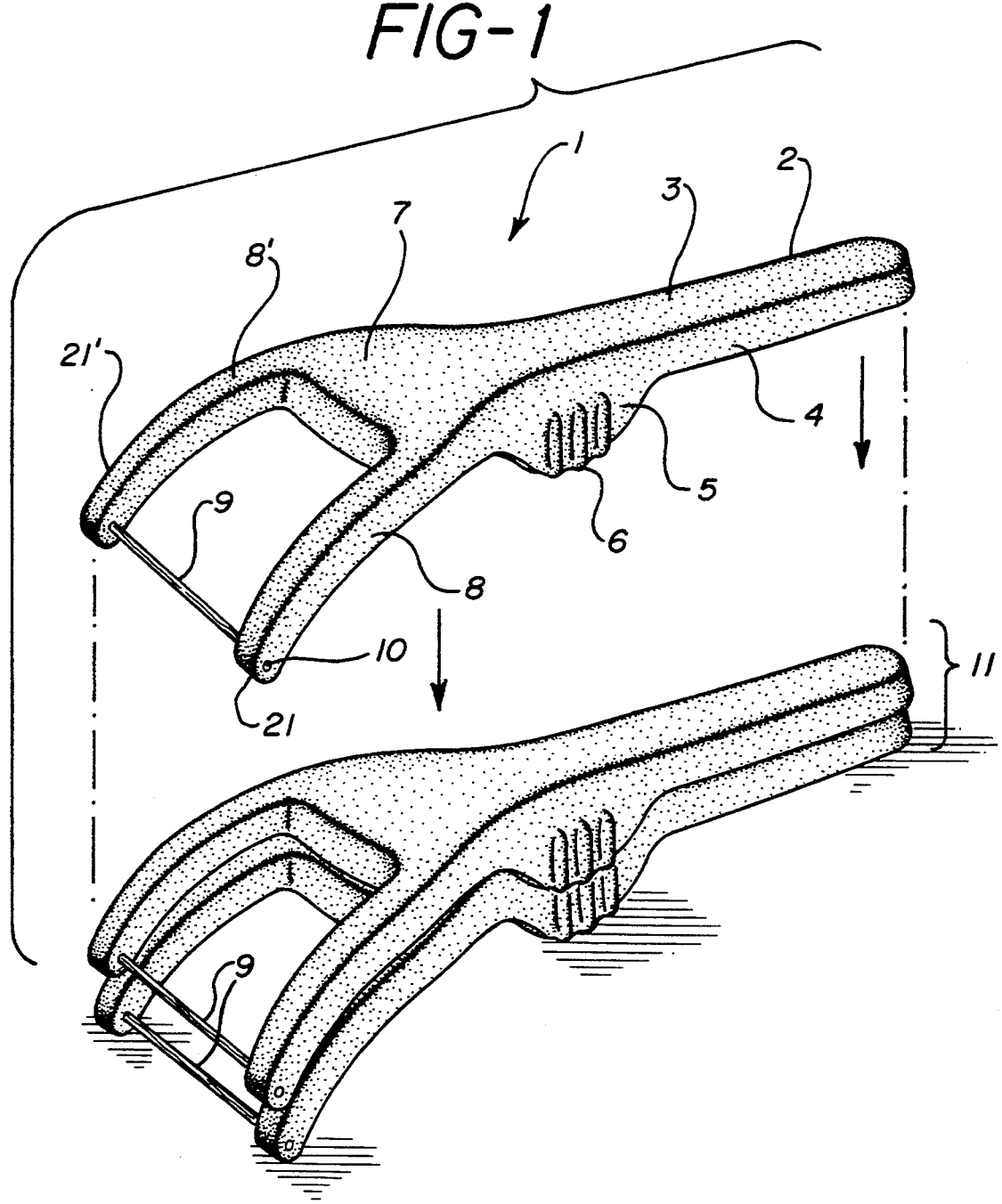
FIG. 1 shows a perspective view of three flossers according to the present invention which are being stacked.

Referring now to the drawing, and in particular to FIGS. 1 through 4, there is shown a flosser 1 according to the present invention. The flosser comprises a handle 2 with a holder 7 affixed to an end thereof. The holder 7 further comprises two protruding arm members 8 and 8'. A strand of dental floss 9 is drawn across between the distal ends 21 and 21' of the arm members 8 and 8'. The floss is anchored 10 into position. The flosser 1 is constructed such that it may be stacked one on top of another as shown by the dotted line in FIG. 1. This stacking is accomplished by directly positioning said flosser on top of an adjacent flosser whereby the two nest, one on top of another without intersecting the general planes of each handle.

Figure 6:
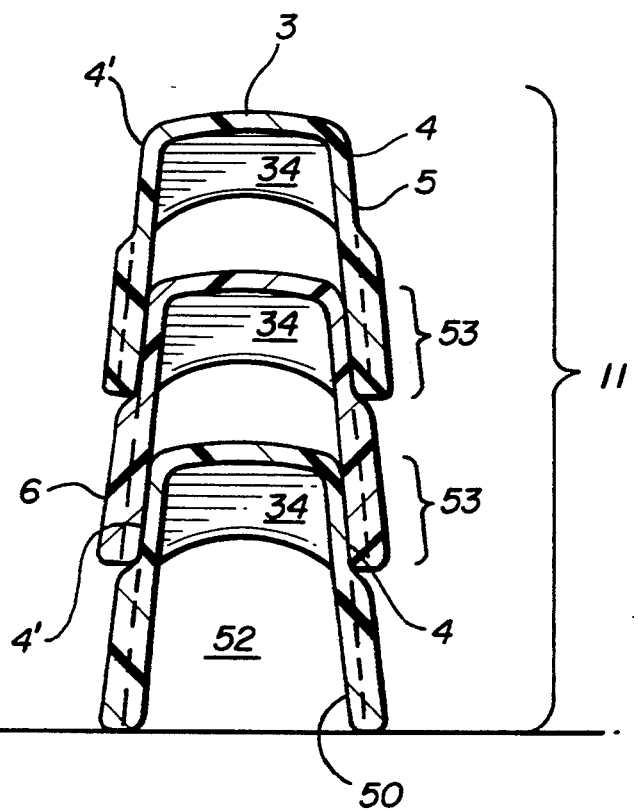
FIG. 6 is an enlarged cross-sectional view of the stack of FIG. 5 cut along line 40—40.

A stack of flossers 11 is shown in FIGS. 1 and 6. As shown in the Figures, the flosser handle is further comprised of an upper surface 3 and side exterior surfaces 4 and 4'. Also affixed to the left and right side surfaces is a protruding wing 5 with protruding finger-grip members 6. These grips 6 provide good tactile feedback to the user. The gripping ribs run width-wise down the side of the handle and are typically parallel. The holder grip 6 can be replaced with a rough mat finish or any other surface known to those skilled in the art to provide sufficient finger gripping.

Figure 5:
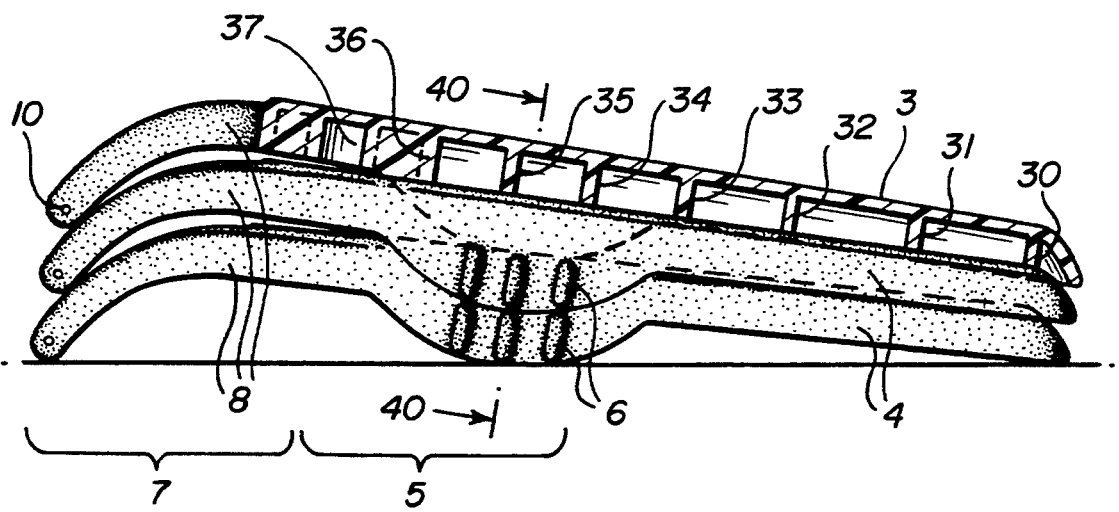
FIG. 5 is a side view of a stack of three flossers, the length-wise cross section of the top flosser has been provided for clarity.

The flosser also comprises a bottom surface 20 which forms a cavity which is complimentary, at least regarding the handle 2, to the upper surface 3 of the flosser. This complimentary nature can be seen in FIGS. 5 and 6. FIG. 6 is a cross-sectional view cut along line 40—40 of three flossers stacked one upon each other. As can be seen, the internal cavity 52 is defined by an interior surface 20 which fits neatly over the outer surface 3 and 4 of the flosser positioned immediately below it. Furthermore, the inner walls 50 of the bottom cavity 52 come into physical contact with an upper region 51 of side wall 4; thus, forming a fit between two stacked flossers. This forms a region of contact 53 which prevents the stack from separating during normal shipping and handling. The fit between the two stacked flossers may be a friction fit. The bond between the inner wall 50 and the top of the outer wall 51 can be enhanced by including snap-lock members, 70 and 71, with complimenting bump and cavity features or, as shown in FIGS. 8 and 9, with bump members on the outer side 71 and inner wall 70 which non-permanently snap-fit to lock the unit together. Preferably the outer bump is captured by the inner wall bump. The snap-lock mechanism is provided on at least one portion of the flosser side 5 and/or wing 4 (See positioning of bumps 70 and 71 on members 51 and 52 in FIGS. 8 and 9). Two snap-fit mechanisms, one on each side, of the flosser is preferred although snap fit mechanisms on the holder and handle end portions of the flosser are also contemplated by the present invention. A non-permanent, snap-fit mechanism is most preferred in the present invention.

The floss portion of the device 9 is typically made of nylon polyamide, Teflon ® polytetrafluoroethylene, Gortex ® polyester or any other biocompatible and medically compatible material. These flosses typically have a denier of from 100 to 2000 and have a length of from about 0.25 inches to about 4 inches. The floss is anchored 10 to arms 8 and 8' by any manner known to those skilled in the art. The anchoring can be permanent or temporary. Methods of affixing the floss which are suitable for the present invention are found in U.S. Pat. No. 3,926,201, issued Dec. 16, 1975 to Katz; U.S. Pat. No. 3,974,842, issued Aug. 17, 1976 to Chodorow; and U.S. Pat. No. 4,006,750, issued Feb. 8, 1977 to Chodorow, all incorporated herein by reference. Thermal-weld anchoring is preferred. Flossers according to the present invention are preferably made of an plastic material such as polypropylene, styrene, polyethylene terephthalate (PET), etc, or mixtures thereof. These materials typically are injection molded. The handle and holder member may be solid; however, in the most preferred construction of the present invention various re-enforcing members, i.e. ribs, are longitudinally positioned along the length of the handle and are strategically positioned along the holder cavity to provide the feel of a solid handle, see 30 through 38. It is important that neither these ribs nor the bottom of a solid handle extend downward to a depth which would interfere and contact the upper surface 3 of a stacked flosser; thus, interfering with the friction fit, if any, in the contact region 53.

Figure 2:
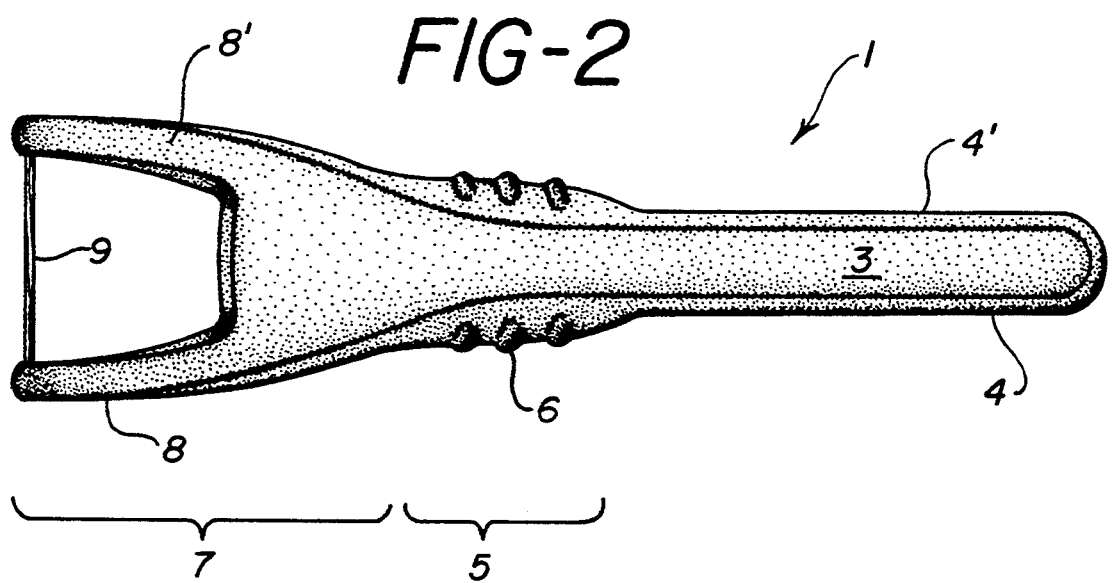
FIG. 2 show a top view of a flosser according to the present invention.
Figure 3:
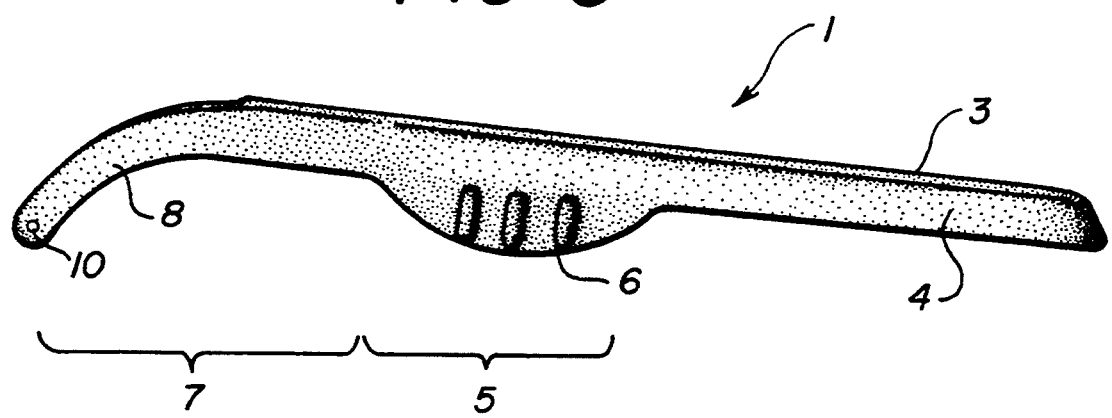
FIG. 3 shows a left side view of the flosser of FIG. 2, the right side view being a mirror image thereof.
Figure 4:
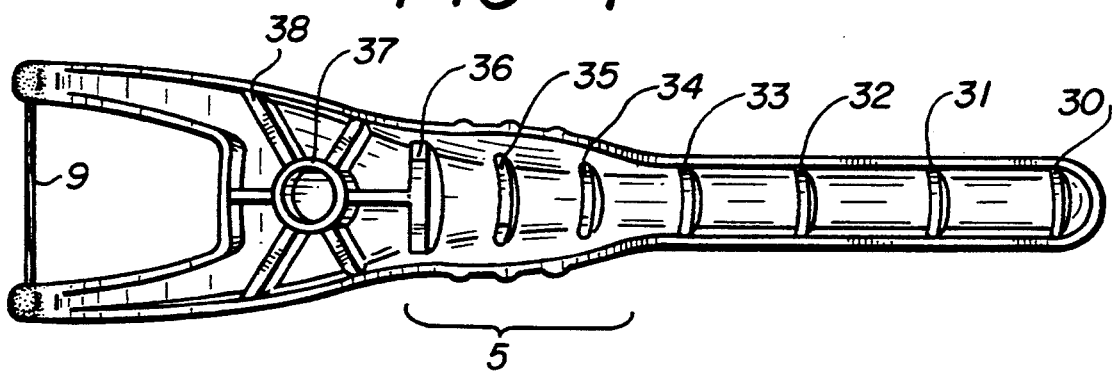
FIG. 4 shows a bottom view of the flosser of FIG. 2.

The complimentary nature of the upper surface of the flosser with the bottom cavity can be seen by comparing FIGS. 2 and 3. As can be seen, the upper surface 3 and 4/4' form a somewhat concave shape which is complimented by the interior cavity 50 formed by the interior surface 20.

The depth and width of the fork formed by the holder 7 may be adjusted by those skilled in the art to provide sufficient penetration between the teeth. Typically, the depth and width are from about 0.25 to about 2 inches.

Figure 7:
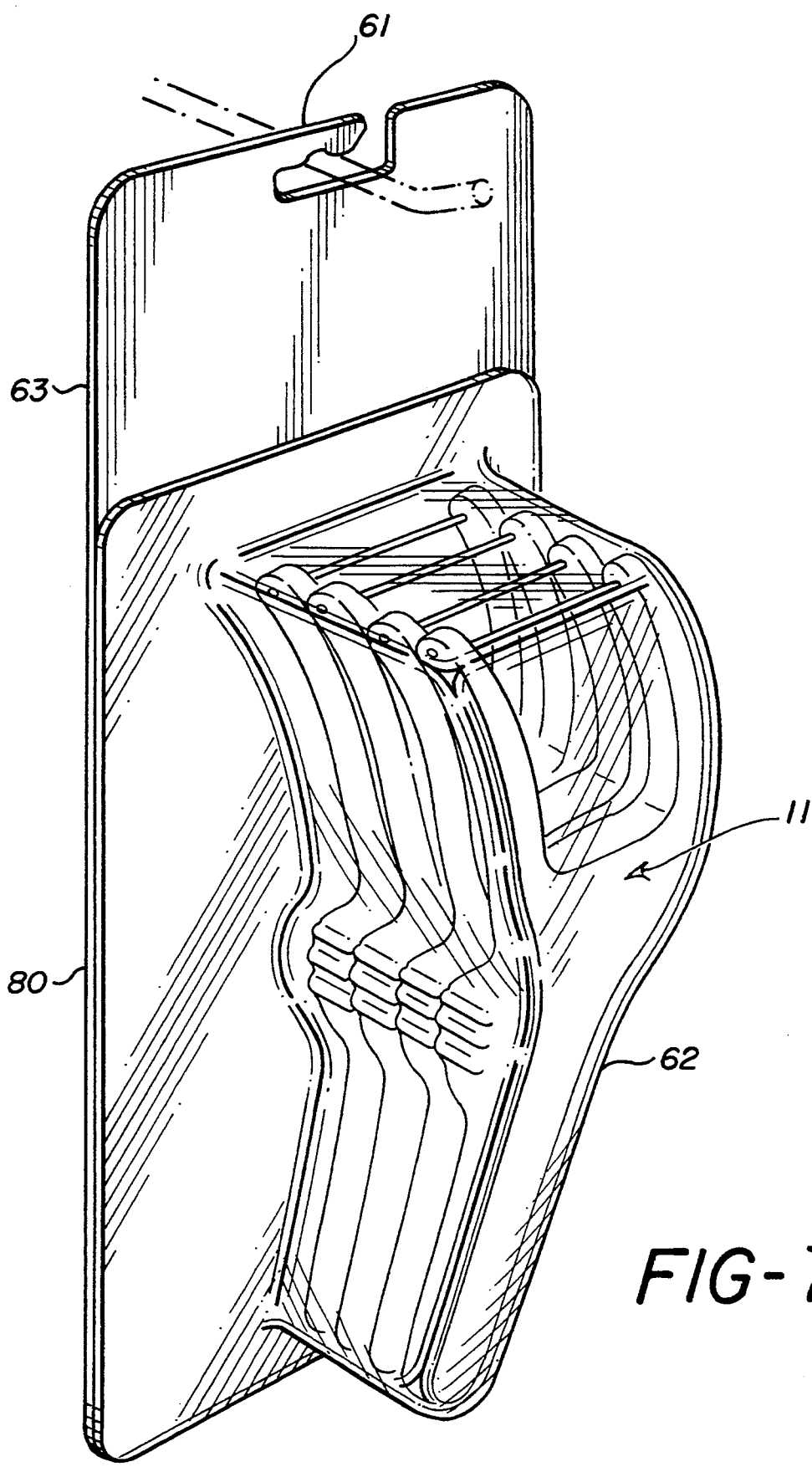
FIG. 7 is a package containing a stack of four flossers.

Referring now to FIG. 7, the present flosser may be stacked such that a plurality of units are fit one on top of the other and nest inside each other. This stack 11 can then be conveniently positioned in a conventional package or in a form fit polyvinyl chloride (PVC) display box 80 as shown in FIG. 7. Optionally, the display box could be a paperboard carton. A PVC display box contains a base 63 on to which a clear PVC cover 62 is placed. The cover 62 compliments the stack and prevents it from unnecessary movement during shipping and handling. Furthermore, this type of packaging better utilizes space (volume) and results in more efficient use of shelf space and packaging materials. This type of package base can also comprise a hook member 61 for placing the package on a display rod.

The arm members are positioned at least parallel to each other. Preferably, the arms form a diverging generally "V" shaped configuration extending outwardly from the handle as can be seen in FIG. 2. As depicted in the Figures, the preferred arm members are arched downward when viewed from the side giving the user a more comfortable angle to insert the floss between the teeth. Other configurations include a straight side view or even an arched up configuration may be used provided that the floss members remain complimentary and do not interfere with a flosser which is stacked below and above it. Preferably, the floss is drawn perpendicular to the general axis of the handle, although other geometries, e.g., diagonal, are within the scope of the present invention.

Although particular embodiments of the present invention have been shown and described, modifications may be make to the present tooth cleaning device without departing from the teachings of the present invention. Accordingly, the present invention comprises all embodiments within the scope of the appended claims.

From the foregoing, it should be evident that the present invention provides a flosser which is portable, compact and easily carried even in a stacked form on the person. It, however, should be understood that the various features disclosed are susceptible to incorporation into other oral care devices without departing from the spirit of the invention. The structure further is one which is simple to manufacture, employing a minimum number of parts which are easily constructed and assembled.

What is claimed is:

1. A tooth cleaning device comprised of a handle, a holder affixed to an end of the handle comprised of two protruding arm members positioned at least parallel to each other and a strand of dental floss which is drawn between the arms and anchored at the distal end of each arm, wherein several tooth cleaning devices may be stacked one on top of another thereby nesting with each other and wherein the handle is further comprised of an upper surface and two side surfaces and a bottom surface which forms a cavity which is complimentary to the upper surface and at least the upper most portion of said side surfaces of the handle.

2. A tooth cleaning device according to claim 1 wherein said bottom surface cavity comprises inner walls which form a friction fit with at least a portion of the side surface of a second tooth cleaning device when the two tooth cleaning devices are stacked one on top of another.

3. A tooth cleaning device according to claim 1 further comprising an upper region of the inner walls of said bottom surface cavity and side surfaces which include snap-lock members to improve the locking nature of the flossers.

4. A tooth cleaning device according to claim 3 wherein each side surface further comprises a protruding wing which forms a finger grip.

5. A tooth cleaning device according to claim 4 wherein said protruding wing further comprises a rough mat finish for enhancing grip.

6. A tooth cleaning device according to claim 4 wherein said protruding wing also comprises a protruding finger grip members.

7. A tooth cleaning device according to claim 6 wherein said floss material is selected from the group consisting of nylon, polytetrafluoroethylene, polyester or mixtures thereof.

8. A tooth cleaning device according to claim 7 wherein said handle and holder are manufactured from a thermoset material selected from the group consisting of polypropylene, styrene or polyethylene terephthalate.

9. A tooth cleaning device according to claim 8 wherein the bottom surface further comprises ribs which are longitudinally positioned along the length of the handle are positioned along the holder cavity wherein further said ribs do not extend downward to a depth which would interfere and contact a second upper surface of the tooth cleaning device.

10. A tooth cleaning device according to claim 9 wherein the depth of the fork formed by the two protruding arms is from about 0.25 to about 2 inches.

11. A stack of a plurality of flossers according to claim 10.

12. A stackable flosser comprised of:
 a. a handle;
 b. a holder positioned at one end of said handle means;
 c. two arms affixed to the holder, distal to said handle;
 d. a strand of dental floss drawn between the arms and anchored thereto; and
 e. a means for non-permanently locking the flosser to another flosser when stacked one on top of the other.

13. A stackable flosser according to claim 12 wherein the handle is further comprised of an upper surface and two side surfaces and wherein the handle further comprises a bottom surface which forms a cavity which is complimentary to the upper surface and at least a portion of said side surfaces of the handle.

14. A tooth cleaning device according to claim 13 wherein said means for non-permanently locking the flosser comprises inner walls which form a friction fit with at least a portion of the side surface of a second tooth cleaning device when the two tooth cleaning devices are stacked one on top of another.

15. A tooth cleaning device according to claim 13 wherein said means for non-permanently locking the flosser comprises inner walls of said bottom surface which include snap-lock members which compliment snap-lock members on the side surface of a second tooth cleaning device.

16. A tooth cleaning device according to claim 15 wherein each side surface further comprises a protruding wing which forms a finger grip.

17. A tooth cleaning device according to claim 16 wherein the bottom surface further comprises ribs which are longitudinally positioned along the length of the handle are positioned along the holder cavity wherein further said ribs do not extend downward to a depth which would interfere and contact said second upper surface of the tooth cleaning device.

* * * * *